(12) United States Patent
Zimmerle et al.

(10) Patent No.: US 9,612,249 B2
(45) Date of Patent: Apr. 4, 2017

(54) REDUCTION OF FALSE POSITIVE ON REAGENT TEST DEVICES

(71) Applicant: Siemens Healthcare Diagnostics Inc., Tarrytown, NY (US)

(72) Inventors: Chris Thomas Zimmerle, Goshen, IN (US); Gary W. Rheinheimer, Goshen, IN (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 0 days.

(21) Appl. No.: 14/767,734

(22) PCT Filed: Feb. 12, 2014

(86) PCT No.: PCT/US2014/016017
§ 371 (c)(1),
(2) Date: Aug. 13, 2015

(87) PCT Pub. No.: WO2014/126995
PCT Pub. Date: Aug. 21, 2014

(65) Prior Publication Data
US 2015/0369827 A1    Dec. 24, 2015

Related U.S. Application Data

(60) Provisional application No. 61/764,905, filed on Feb. 14, 2013.

(51) Int. Cl.
*G01N 21/78* (2006.01)
*G01N 33/72* (2006.01)
(Continued)

(52) U.S. Cl.
CPC ......... *G01N 33/728* (2013.01); *G01N 21/253* (2013.01); *G01N 21/78* (2013.01); *G01N 21/274* (2013.01); *Y10T 436/146666* (2015.01)

(58) Field of Classification Search
CPC ...... G01N 33/728; G01N 33/72; G01N 33/50; G01N 33/48; G01N 21/78; G01N 21/77;
(Continued)

(56) References Cited

U.S. PATENT DOCUMENTS

| 3,123,443 A | 3/1964 | Smeby et al. |
| 3,212,855 A | 10/1965 | Mast et al. |

(Continued)

FOREIGN PATENT DOCUMENTS

| EP | 2579035 A1 | 4/2013 |
| JP | H07035744 A | 2/1995 |

(Continued)

OTHER PUBLICATIONS

International Search Report and Written Opinion of International Application No. PCT/US2014/016017 dated May 16, 2014.
(Continued)

*Primary Examiner* — Christine T Mui
(74) *Attorney, Agent, or Firm* — Kyle D. Petaja

(57) ABSTRACT

Methods and systems are disclosed including a reagent analyzer, comprising a test analyzing mechanism, such as an optical imaging system, configured to read a first sample of a specimen combined with a reagent configured to react with the sample in a presence of an analyte of interest and a second sample of the specimen that is not combined with a reagent, and to output one or more first signals indicative of the test analyzing mechanism reading the first and second samples; and a processor receiving the one or more first signals and executing logic to analyze the second sample responsive to the processor determining that the analyte of interest is present in the first sample. The processor may execute logic to analyze the second specimen utilizing one
(Continued)

or more ratio algorithm and comparing the results of the algorithm against predetermined values indicative of expected color.

15 Claims, 3 Drawing Sheets

(51) Int. Cl.
*G01N 21/25* (2006.01)
*G01N 21/27* (2006.01)

(58) Field of Classification Search
CPC ...... G01N 21/75; G01N 21/00; Y10T 436/14; Y10T 436/146666; Y10T 436/145555; Y10T 436/00
USPC .............................................. 436/97, 96, 91
See application file for complete search history.

(56) References Cited

U.S. PATENT DOCUMENTS

| | | |
|---|---|---|
| 3,814,668 A | 6/1974 | Blake et al. |
| 4,526,753 A | 7/1985 | Boger et al. |
| 5,449,622 A | 9/1995 | Yabe et al. |
| 2006/0257284 A1 | 11/2006 | Rheinheimer et al. |
| 2008/0070318 A1 | 3/2008 | Yamamoto et al. |
| 2012/0046203 A1 | 2/2012 | Walsh et al. |
| 2013/0041236 A1 | 2/2013 | Pugia et al. |
| 2013/0079236 A1 | 3/2013 | Holmes |
| 2013/0157372 A1 | 6/2013 | Galano et al. |
| 2013/0162981 A1 | 6/2013 | Emeric et al. |

FOREIGN PATENT DOCUMENTS

| | | |
|---|---|---|
| WO | 2011137039 A1 | 11/2011 |
| WO | 2011152238 A1 | 12/2011 |
| WO | 2013090655 A1 | 6/2013 |

OTHER PUBLICATIONS

European Search Report and Written Opinion of European Application No. EP14751345.1, dated Jan. 31, 2017.

REDUCTION OF FALSE POSITIVE ON REAGENT TEST DEVICES

CROSS REFERENCE TO RELATED APPLICATIONS

This application claims benefit under 35 U.S.C. 119(e) of provisional application U.S. Ser. No. 61/764,905, filed Feb. 14, 2013, the entire contents of which are hereby expressly incorporated herein by reference.

FIELD OF THE DISCLOSURE

The disclosure generally relates to analyzers for reagent cards, and more particularly, but not by way of limitation, to methods and systems for the reduction of false positive readings in analyzers of multi-profile reagent cards.

BACKGROUND

Reagent test strips are widely used in many fields, including the fields of medicine and clinical chemistry. A reagent test strip usually has one or more reagent test areas, and each reagent test area is capable of undergoing a color change in response to contact with a liquid specimen. The liquid specimen usually contains one or more constituents, substances, or properties of interest. The presence and concentrations of these constituents of interest in the specimen are determinable by an analysis of the color changes undergone by the reagent test strip. Usually, this analysis involves a color comparison between the reagent test area or reagent test pad and a standard color or color scale, such as a color wheel. In this way, reagent test strips assist physicians in diagnosing diseases and other health problems, for example.

To satisfy the needs of the medical profession, as well as other expanding technologies, such as the brewing industry, chemical manufacturing, etc., a myriad of analytical procedures, compositions, and tools have been developed, including the so-called "dip-and-read" type reagent test devices. Regardless of whether dip-and-read test devices are used for the analysis of a biological fluid or tissue, or for the analysis of a commercial or industrial fluid or substance, the general procedure involves a reagent test device coming in contact with the sample or specimen to be tested, and manually or instrumentally analyzing the reagent test device.

Dip-and-read reagent test devices can be manufactured at relatively low cost and are very convenient for individuals to use. Consequently dip-and-read reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a dip-and-read reagent test device into a sample of body fluid or tissue, such as urine or blood, (or by applying the sample to the reagent test device) and observing a detectable response, such as a change in color and/or a change in the amount of light reflected from, or absorbed by the test device.

Many analysis systems for reagent test devices for detecting body fluid components are capable of making quantitative, or at least semi-quantitative, measurements. Thus, by measuring the detectable response after a predetermined time, a user can obtain not only a positive indication of the presence of a particular constituent in a test sample, but also an estimate of how much of the constituent is present. Such dip-and-read reagent test devices provide physicians and laboratory technicians with a facile diagnostic tool, as well as with the ability to gauge the extent of disease or of bodily malfunction.

Illustrative of dip-and-read reagent test devices currently in use are products available from Siemens Healthcare Diagnostics Inc. under the trademark MULTISTIX, and others. Immunochemical, diagnostic, or serological test devices such as these usually include one or more carrier matrix, such as absorbent paper, having incorporated therein a particular reagent or reactant system which manifests a detectable response (e.g., a color change) in the presence of a specific test sample component or constituent. Depending on the reactant system incorporated with a particular matrix, these reagent test devices can detect the presence of substances such as glucose, ketone bodies, bilirubin, urobilinogen, occult blood, nitrite, and other substances. A specific change in the intensity of color observed within a specific time range after contacting the reagent test device with a sample is indicative of the presence of a particular constituent and/or its concentration in the sample. Some other examples of reagent test devices and reagent systems may be found in U.S. Pat. Nos. 3,123,443; 3,212,855; and 3,814,668.

Testing tools and methods have been sought in the art for economically and rapidly conducting multiple tests, especially via using automated processing. Automated analyzer systems have an advantage with respect to cost per test, test handling volumes, and/or speed of obtaining test results or other information over manual testing.

A recent development is the introduction of multiple-profile reagent cards and multiple-profile reagent card automated analyzers. Multiple-profile reagent cards are essentially card-shaped test devices which include a substrate and multiple reagent-impregnated pads (or matrices), and/or blank test pads (also known as color pads) without reagents, positioned onto the substrate, for simultaneously or sequentially performing multiple analyses of analytes, such as the one described in U.S. Pat. No. 4,526,753, for example, the entire disclosure of which is hereby expressly incorporated herein by reference.

Multiple-profile reagent cards result in an efficient, economical, rapid, and convenient way of performing automated analyses. Automated analyzers configured to use multiple-profile reagent cards typically take a multiple-profile reagent card, such as from a storage drawer, or a cassette, and advance the multiple-profile reagent card through the analyzer over a travel surface via a card moving mechanism. The card moving mechanism may be a conveyor belt, a ratchet mechanism, a sliding ramp, or a card-gripping or pulling mechanism, for example. As the multiple-profile reagent card is moved or travels along the travel surface, one or more sample dispensers (e.g., manual or automatic pipette or pipette boom) may deposit or dispense one or more samples or reagents onto one or more of the reagent pads. Next, the multiple-profile reagent card may be analyzed (e.g., manually or automatically) to gauge the test result, such as via an optical imaging system, a microscope, or a spectrometer, for example. Finally, the used reagent card is removed from the analyzer, and is discarded or disposed of in an appropriate manner, such as a waste receptacle.

However, in some instances the detectable response of the reagent pad and the specimen results in one or more false positive results indicating the detection of the constituent, such as an analyte, in the specimen. To that end, a need exists in the prior art for systems and methods to reduce the occurrence of false positive results. It is to such analytical detection and verification systems and methods that the inventive concepts disclosed herein are directed.

SUMMARY

A method and system are disclosed. The problem of an undesirable level of false positive results indicating the detection of a constituent, such as an analyte, in a first sample of a specimen when no such constituent is present is addressed through a methodology and system for verifying the presence of the constituent in a second sample of the specimen by analyzing the second sample with a separate form of logic to verify the presence of the constituent.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals are intended to refer to the same or similar elements for consistency. For purposes of clarity, not every component may be labeled in every drawing. Certain features and certain views of the figures may be shown exaggerated and not to scale or in schematic in the interest of clarity and conciseness. In the drawings.

DETAILED DESCRIPTION

Figure 1:
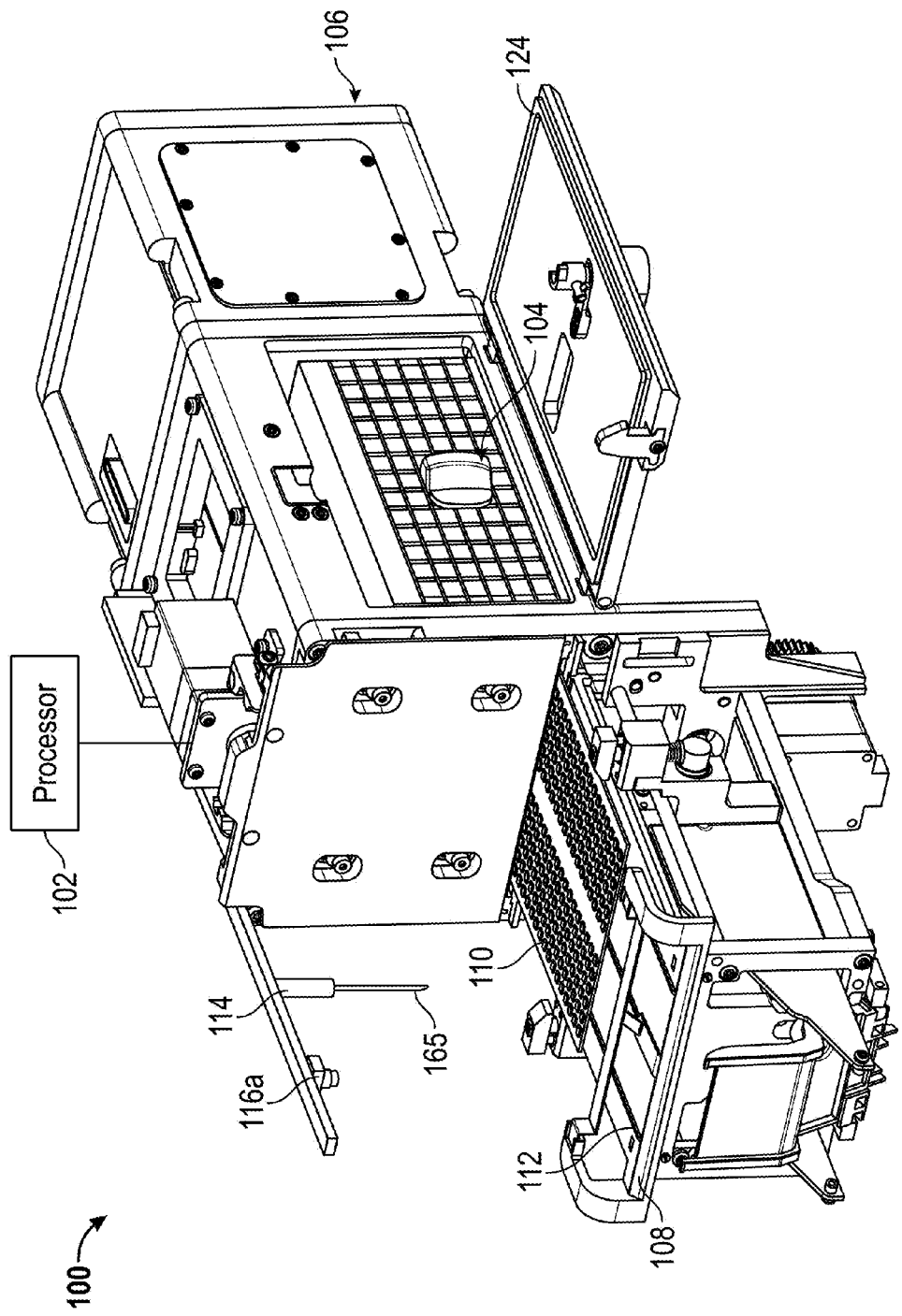
FIG. 1 is a perspective view of an exemplary analyzer and reagent card in accordance with the present invention.

The following detailed description refers to the accompanying drawings. The same reference numbers in different drawings may identify the same or similar elements.

The mechanisms proposed in this disclosure circumvent the problems described above. In one embodiment, a reagent analyzer comprises a test analyzing mechanism configured to read at least one property of a first sample of a specimen combined with a reagent and a second sample of the specimen (which may be combined with another reagent or may not be combined with any reagent), and to output one or more first signals indicative of the test analyzing mechanism reading the first sample combined with the reagent and the test analyzing mechanism reading the second sample.

The reagent analyzer further comprises a processor receiving the one or more first signals indicative of the reading of the first sample combined with the reagent and the reading of the second sample. The processor may execute first logic to analyze the one or more first signals to determine whether an analyte of interest is present in the first sample by quantifying a first predetermined property of the first sample combined with the reagent. The processor may execute second logic to analyze the one or more first signals to quantify a second predetermined property of the second sample. The processor may execute third logic to verify the presence of the analyte of interest in the first sample based on the quantification of the first predetermined property and the second predetermined property, such as color. The test analyzing mechanism may be an optical imaging system receiving one or more first reflectance signals having wavelengths of light from the first sample and the second sample, and wherein the first and second predetermined properties of the first and second samples are a measure of colors or color ranges represented by the wavelengths.

In one embodiment, a reagent analyzer comprises a test analyzing mechanism configured to read a first sample combined with a reagent and a second sample that is not combined with the reagent, and to output one or more first signals indicative of the test analyzing mechanism reading the first and second samples. The reagent analyzer may further comprise a processor receiving the one or more first signals indicative of the reading of the first sample combined with the reagent, and executing first logic to analyze the second sample within the one or more first signals responsive to the processor determining that an analyte of interest is present in the first sample. The test analyzing mechanism may be an optical imaging system receiving one or more reflectance signals having wavelengths of light from the first sample and the second sample and wherein the one or more first signals is indicative of the optical imaging system reading the first and second samples and determining colors or color ranges represented by the wavelengths of light.

In one embodiment, the optical imaging system may generate one or more images having pixels with each pixel comprising information indicative of core components, such as red, blue, and green color wavelength regions, the one or more image having a first region of pixels indicative of wavelengths of light reflecting from the first sample, and a second region of pixels indicative of wavelengths of light reflecting from the second sample. The processor may execute logic to analyze the first sample to verify the presence of the analyte of interest in the first specimen utilizing a ratio algorithm. The analyte of interest may be bilirubin and the ratio algorithm may be 1000*((red RGB code)/(RGB code+30)). The processor may execute logic to compare the results of the ratio algorithm to a known value indicative of an expected color or expected color range.

DESCRIPTION

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As discussed above, currently, false positive results from reagent analyzers may indicate the detection of a constituent, such as an analyte, in a sample of a specimen when no such constituent is present. In one embodiment, the present disclosure addresses these deficiencies with a methodology and system for verifying the presence of the constituent in a first sample of the specimen by analyzing a second sample of the specimen on a non-reagent test pad utilizing a ratio algorithm, taking into consideration a color of the specimen.

In one embodiment, the color of the first sample of the specimen combined with a reagent may be compared to a standard color, such as a color chart or color wheel, for the first sample, having the constituent present, in reaction to a first reagent. The colors may be translated into numerical values for color components representing the reflected wavelengths, for example in RGB code, as is well known in the art. If the comparison indicates the first sample of the specimen contains the constituent of interest, then analysis of a second sample of the specimen without the presence of the reagent may be automatically executed to verify the finding. Specifically, a confirmatory ratio algorithm (or other algorithm) may be utilized to analyze one or more reflectance signal from the second sample of the specimen without the presence of the first reagent. The result of the confirmatory ratio algorithm (or other algorithm) may be analyzed to determine if the result falls within a standard expected range, and if so, the finding that the first sample of the specimen contains the constituent of interest is verified.

Referring now to FIG. 1, shown therein is a perspective view of an exemplary embodiment of an automatic reagent analyzer 100 according to the inventive concepts disclosed herein. Generally, the automatic reagent analyzer 100 may include a processor 102, a storage compartment 104, a card stripping assembly 106, a card travel assembly 108 configured to move a reagent card 110 along a travel surface 112 past a sample delivery assembly 114 and past a test analyzing mechanism 116, such as an optical imaging system 116a. The automatic reagent analyzer 100 may also include a waste ramp assembly and a waste receptacle (not shown), for example for disposing of the reagent cards 110 after the reagent cards 110 have been read by the test analyzing mechanism 116. Automatic reagent analyzers are further described in U.S. patent application Ser. No. 13/712,144 filed on Dec. 12, 2012, and in PCT application number PCT/US2012/069621 filed on Dec. 14, 2012, which are hereby expressly incorporated herein by reference in their entirety.

The processor 102 may be located anywhere within the automatic reagent analyzer 100. The processor 102 may be implemented as a single processor or multiple processors working together or independently to execute processor executable code implementing the logic described herein to reduce the occurrence of false positives. Embodiments of the processor 90 may include a digital signal processor (DSP), a central processing unit (CPU), a microprocessor, a multi-core processor, an application specific integrated circuit, a field programmable gate array and combinations thereof. The processor 90 may include or be coupled to a non-transitory computer readable medium. The non-transitory computer readable medium can be implemented as RAM, ROM, flash memory or the like, and may take the form of a magnetic device, optical device or the like. The non-transitory computer readable medium can be a single non-transitory computer readable medium, or multiple non-transitory computer readable mediums functioning logically together or independently. The processor executable code can be stored in the non-transitory computer readable medium, read by the processor 102 and executed to perform the logic described herein to reduce the occurrence of false positives.

The storage compartment 104 may be configured to accept a reagent card cassette having one or more reagent cards 110, such as one or more multiple-profile reagent cards 110. The card stripping assembly 106 may be configured to strip, eject, advance, or otherwise remove one or more reagent card 110 from the storage compartment 104 (e.g., from a cassette or from a stack of reagent cards 110), and advance such reagent card 110 to the card travel assembly 108. The card travel assembly 108 may be a conveyor belt, a ratchet mechanism, a sliding ramp, or a card-gripping or pulling mechanism, for example. An optional external housing (not shown) may be implemented to house and protect the various components of the automatic reagent analyzer 100, and to protect technicians and laboratory work surfaces from contamination, for example.

Figure 2:
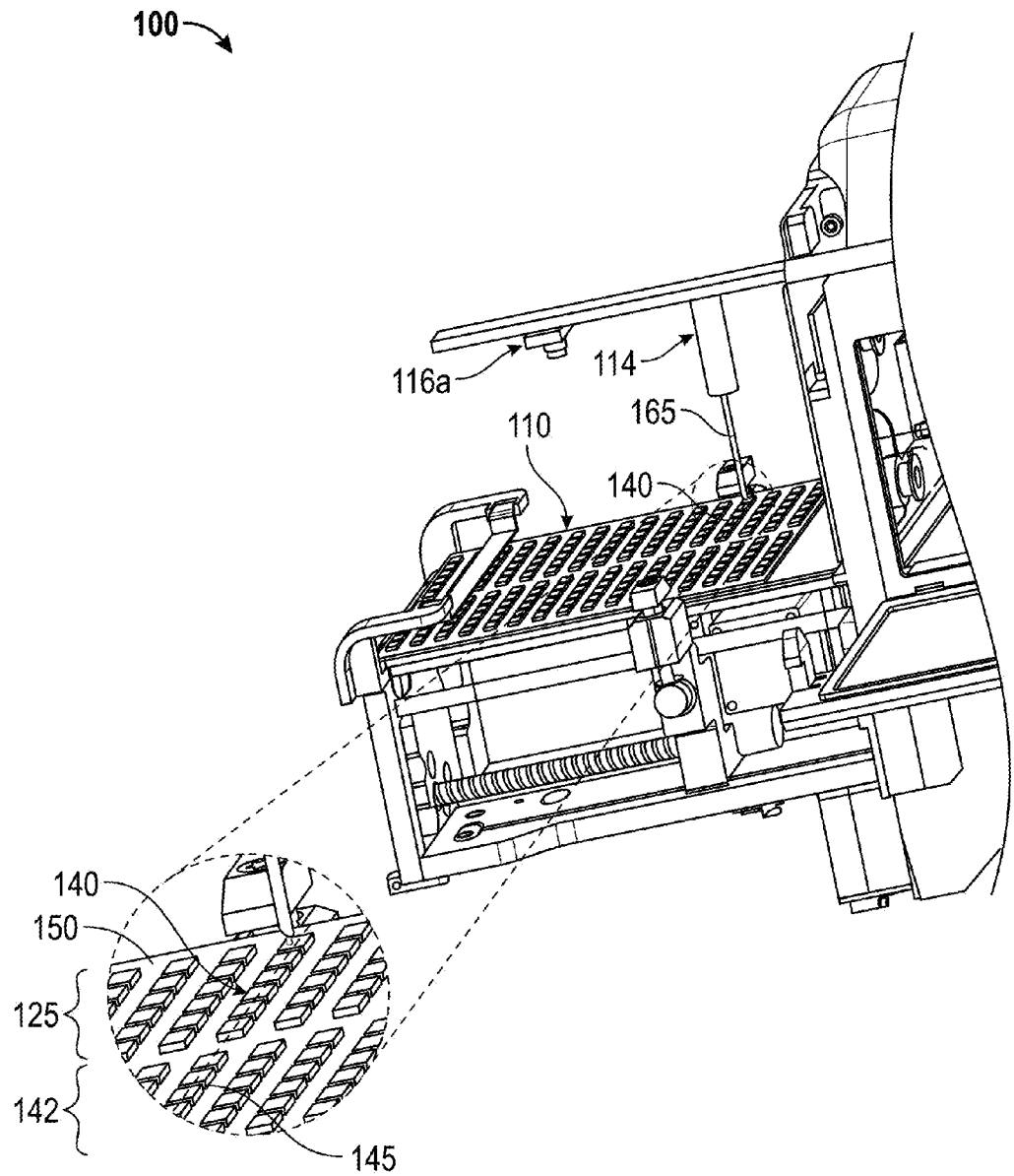
FIG. 2 is a perspective view of a portion of the exemplary analyzer and a magnified view of the reagent card in accordance with the present invention.

Referring now to FIG. 2, the reagent card 110 may include a plurality of reagent areas 125. In one embodiment, the reagent areas 125 include one or more reagent pads 140. In another embodiment, the reagent areas 125 include fluidic compartments (not shown), for example, in microfluidic devices. Microfluidic devices are described in more detail in U.S. patent application Ser. No. 13/643,633, filed on Oct. 26, 2012 (corresponding to PCT application number PCT/US2011/033556, filed on Apr. 22, 2011), titled "SAMPLE ANALYSIS SYSTEM AND METHOD OF USE," which is incorporated herein by reference in its entirety.

The reagent card 110 may have one or more test regions 142 that do not contain a reagent, such as test pad 145, which may also be known as color pad 145. The test pad 145 may be designed so as to not react with the sample of the specimen so that the color of the specimen may be determined. The reagent pads 140 and test pads 145 may be spaced apart a distance from one another so that the test regions 142 are spaced apart within the image(s) of the reagent card 110. The reagent card 110 may be a multiple-profile reagent card 110 having multiple reagent areas 125 and/or test regions 142, such as multiple reagent pads 140 and/or multiple test pads 145.

The one or more reagent card 110 may include a substrate 150 and may have one or more reagent pads 140 and/or test pads 145 positioned and attached thereon. Each reagent pad 140 and test pad 145 may be capable of undergoing a color change in response to contact with a sample of a specimen. The specimen may be a liquid such as urine, saliva or blood. The liquid specimen may contain one or more constituents or properties of interest such as bilirubin. For example, the one or more constituents may be one or more analytes. The presence and concentrations of these constituents of interest in the specimen may be determinable by an analysis of the color changes undergone by the one or more reagent pads 140 and/or test pads 145 at predetermined times after application of the samples to the reagent pads 140 and/or test pads 145. This analysis may involve a color comparison between the reagent pads 140 and/or test pads 145 to each other at different time periods after application of the sample and/or with a color standard or scale. In this way, the reagent card 110 may assist in diagnosing the existence of diseases and other health problems.

The reagent areas 125, such as reagent pads 140, may be provided with different reagents for detecting the presence of different constituents. Different reagents may cause one or more color change in response to the presence of a certain type of constituent in the specimen, such as a certain type of analyte. The color developed by a reaction of a particular analyte with a particular reagent may define the characteristic discrete spectrum for absorption and/or reflectance of light for that particular analyte. The extent of color change of the reagent and the sample of the specimen may depend on the amount of the constituent present in the sample of the specimen.

When the reagent card 110 is advanced over the travel surface 112, a volume of sample may be dispensed onto a central region of the one or more reagent pad 140 and/or test pad 145 by the sample delivery assembly 114, which may comprise, for example a sample dispenser 165. One or more pipettes (e.g., manual or automatic) of the sample delivery assembly 114 may deposit one or more samples and/or reagents onto the reagent pads 140 and/or test pads 145 of the reagent card 110, and then the reagent card 110 may be read by the test analyzing mechanism 116, such as the optical imaging system 116a, for example. Further, in some exemplary embodiments the sample delivery assembly 114 may include one or more sample delivery mechanisms, such as an automatic pipette operated by a robotic arm, a manual pipette, and combinations thereof, in order to deposit a sample onto reagent pads 140 and/or test pads 145 of the reagent card 110. The test analyzing mechanism 116 (e.g., optical imaging system 116a) and the sample delivery assembly 114 may be controlled and read by the processor 102, for example.

Further, the test analyzing mechanism 116, such as optical imaging system 116a, may take one or more images of the one or more reagent card 110 at any time interval after the volume of sample has been dispensed on the one or more reagent pad 140 and/or test pad 145, and regardless of the location of the reagent card 110 on the travel surface 112, for example. In one exemplary embodiment, a video, or a sequence of images may be taken of the one or more reagent pad 140 and/or test pad 145 at a variety of time intervals after the volume of sample is deposited on the one or more reagent pad 140 and/or test pad 145 as the one or more reagent card 110 is advanced along the travel surface 112.

The optical imaging system 116a may be implemented and function as any desired reader, and may be supported at a location above the travel surface 112, so that an image of the reagent pads 140 and/or test pads 145 may be captured by the optical imaging system 116a, for example. Each image may depict the reagent pads 140 and the test pads 145, for example. The optical imaging system 116a may take an image of a reagent pad 140 and/or test pad 145 at any desired target location or area along the travel surface 112, or any other desired location or area or multiple locations or areas, for example.

The optical imaging system 116a may include any desired digital or analog imager, such as a digital camera, an analog camera, a CMOS imager, a diode, and combinations thereof. The optical imaging system 116a may also include any desired illumination source and/or lens system, for example. Further, the optical imaging system 116a is not limited to an optical imaging system in the visible spectrum, and may include a microwave imaging system, an X-ray imaging system, and other desired imaging systems, for example.

Non-exclusive examples of the optical imagining system 116a include optical imaging systems, spectrophotometers, gas chromatographs, microscopes, IR sensors, and combinations thereof, for example. In one embodiment, the optical Imaging system 116a may include the processor 102 and be configured to gauge test results as one or more multiple-profile reagent card 110 is advanced through the automatic reagent analyzer 100.

The optical imaging system 116a may determine the color of a sample of the specimen, which may be urine disposed on the one or more reagent pads 140 and/or test pad 145 by illuminating the reagent card 110 and taking one or more reflectance readings from the reagent pads 140 and/or test pad 145. Each reflectance reading may have a magnitude relating to a different wavelength of light (i.e. color). The color of the sample(s) of the specimen and/or the specimen reaction with one or more reagents in the one or more reagent areas may be determined based upon the relative magnitudes of the reflectance signals of various color components, for example, red, green, and blue reflectance signals. The color may be translated into a standard color code, which typically includes three or four values or color components (e.g. RGB code and CMYK code) whose combination represents a particular color.

Based upon an analysis of the magnitude of the reflectance signal generated by the optical imaging system 116a, the processor 102 may assign the sample to one of a number of categories, e.g., a first category corresponding to no constituent present in the sample, a second category corresponding to a small concentration of constituent present in the sample, a third category corresponding to a medium concentration of constituent present in the sample, and a fourth category corresponding to a large concentration of constituent present in the sample.

However, in some situations, the processor 102 may categorize the sample of the specimen as containing the constituent when, in fact, the sample of the specimen does not contain the constituent—a situation known as a "false positive" reading. For example, if the sample of the specimen is a color that reacts with the reagent to produce a color consistent with the color produced when the constituent is present, the specimen may be flagged as containing the constituent based on the color. In order to circumvent this problem, the inventive system and method in accordance with the present disclosure may be utilized to analyze a second sample of the specimen without a presence of the reagent using one or more confirmatory algorithm.

In one embodiment, the sample delivery assembly 114 may deposit a first sample of the specimen on the reagent pad 140 and a second sample of the specimen on the test pad 145. The test analyzing mechanism 116, such as the optical imaging system 116a, may receive and read one or more reflectance signals, having wavelengths of light, from the first sample of the specimen that is combined with the reagent on the reagent pad 140. The optical imaging system 116a may also receive and read one or more reflectance signals, having wavelengths of light, from the second sample of the specimen on the test pad 145. Of course, the second sample of the specimen may be on a second reagent pad 140 that contains a different reagent from the first reagent pad 140 rather than the test pad 145.

The test analyzing mechanism 116, such as the optical imaging system 116a, may output one or more first signals (which may be one or more images) indicative of reflectance and/or absorption of light from the first sample of the specimen combined with the reagent on the reagent pad 140 and the second sample of the specimen on the test pad 145, for example. The processor 102 may receive the one or more first signals indicative of the reading of the first sample combined with the reagent on the reagent pad 140 and the reading of the second sample on the test pad 145. The processor 102 may execute logic to analyze the first sample of the specimen combined with the reagent on the reagent pad 140 to quantify a first predetermined property, such as color, of the first sample of the specimen combined with the reagent and to determine whether an analyte of interest is present in the first sample of the specimen by, for example, comparing the quantified color to a known standard.

The processor 102 may execute second logic to analyze the second sample of the specimen represented in the one or more first signals to quantify a second predetermined property, such as an expected color or color range, of the second sample of the specimen. The one or more first signals may be an image having pixel values which may be interpreted by a suitable color code, such as RGB, as discussed above. In this example, the second logic may include a ratio algorithm in which one of the components of the color code is the numerator and another one of the components of the color code is the denominator. The ratio algorithm enhances or magnifies the discrimination between the two components of the color code to aid in detecting the constituent. The processor 102 may execute logic to verify the presence of the analyte of interest in the specimen based on the quantification of the first predetermined property and the second predetermined property. For example, the processor 102 may compare the color of the first sample of the specimen in reaction to the reagent to a known standard and may compare the result of the ratio algorithm of the second sample of the specimen to another known standard. A positive result of both comparisons, utilizing the two different standards, verifies the positive finding of the constituent in the specimen.

Of course, it should be understood that the test analyzing mechanism 116 may be used to read any property of the specimens, not necessarily color, and output one or more signals indicative of the reading.

Figure 3:
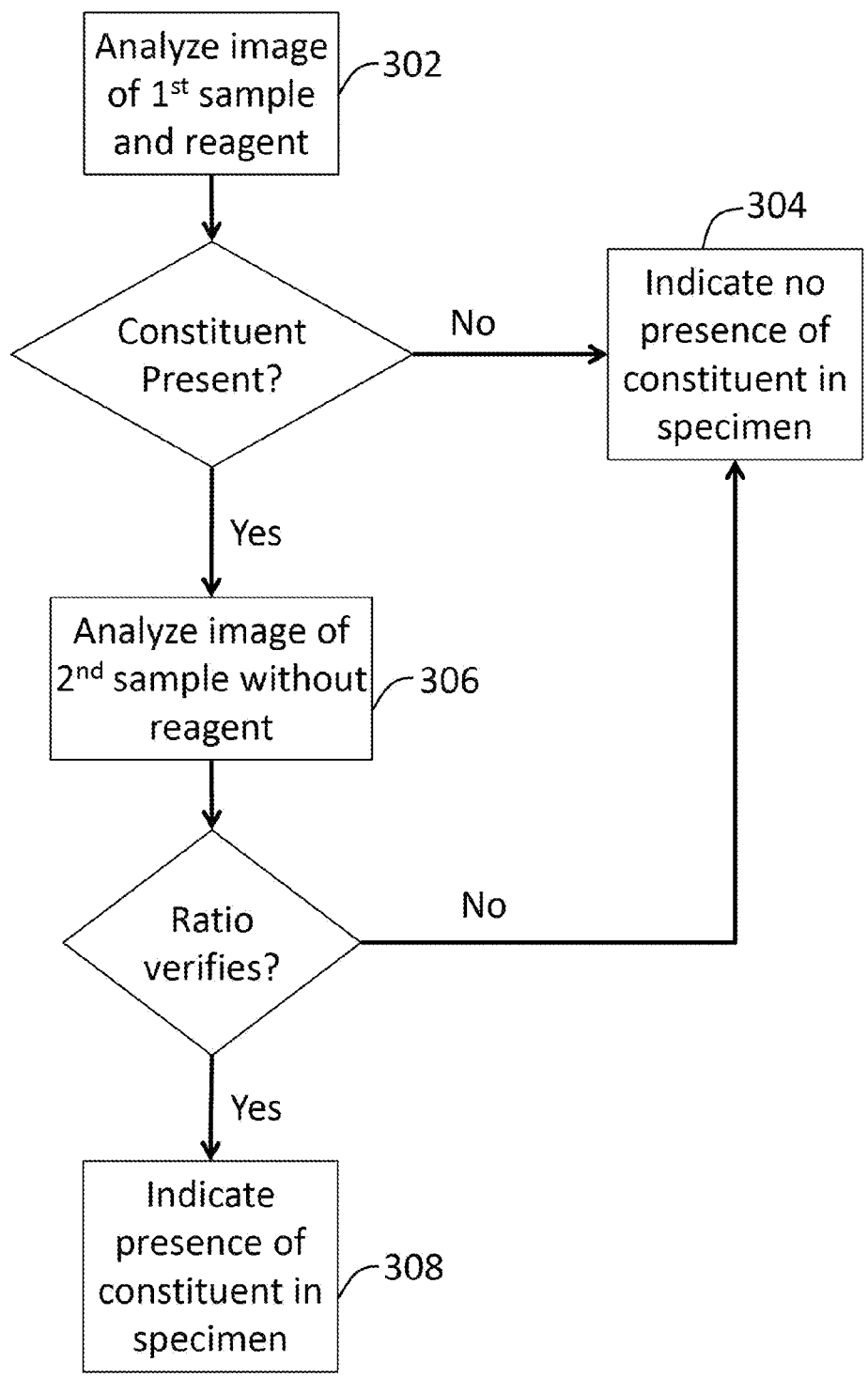
FIG. 3 is a flow diagram of an exemplary process in accordance with the present invention.

Shown in FIG. 3 is an exemplary process 300 that may be executed by the processor 102 in order to reduce the occurrence of false positive results. In one aspect of the present invention, the processor 102 may analyze the second sample of the specimen on the test pad 145 responsive to the results of the analysis of the first sample of the specimen. For example, as illustrated in the flowchart of FIG. 3, the processor 102, in step 302, analyzes the one or more image and determines whether the constituent of interest, for example, bilirubin, is present in the first sample of the specimen by utilizing first logic such as a ratio algorithm of color components of the pixels within the one or more images and comparing a numerical result to a first predetermined numerical scale. If the comparison indicates that the bilirubin is not present, the processor 102 branches to a step 304 and stores information and/or outputs a signal indicating that the specimen does not contain bilirubin (a negative result) in and the process stops. However, if the comparison indicates that bilirubin is present (a positive result), the processor 102 branches to a step 306 in order to analyze the second sample of the specimen. The analysis of the second sample of the specimen can be accomplished by utilizing another ratio algorithm of color components of the pixels within the one or more images and comparing the numerical result to a second predetermined numerical scale, as in step 306. If the comparison indicates that bilirubin is present (a positive result), the processor 102 stores information and/or outputs a signal indicating that the specimen is positive for bilirubin, in step 308. If the comparison indicates that the bilirubin is not present, the processor 102 indicates (e.g., stores information or outputs a signal) that the specimen does not contain bilirubin (a negative result overriding the first false positive result) in step 304 and the process stops.

In one embodiment, as part of the optical imaging system 116a reading the first and second samples of the specimen, the optical imaging system 116a may generate one or more image of the reagent card 110, the images having pixels. Each pixel may comprise information indicative of color components, such as red, blue, and green color wavelength regions. Of course, depending on the imaging system used, different color models may be used such as CMYK. One region of the pixels of the one or more image may be indicative of wavelengths of light reflecting from the first sample of the specimen on the reagent pad 140. Another region of the pixels of the one or more image may be indicative of wavelengths of light reflecting from the second sample of the specimen on the test pad 145.

The processor 102 may execute logic to utilize the ratio algorithm in order to reduce the possibility of producing a false positive result. The processor 102 may utilize the ratio algorithm to analyze the wavelengths of the reflectance signal of the second sample of the specimen on the test pad 145 producing a numeric result indicative of color of the specimen. The processor 102 may compare the numeric result with a predetermined scale of expected numeric results.

For example, bilirubin is a highly colorimetric substance whose presence in urine tends to make the urine a dark amber or brown color. In this instance, the blue wavelength component of the reflectance signal decreases and the red wavelength component of the reflectance signal tends to remain constant when compared to urine samples without bilirubin. Generally, the peak absorbance of a bilirubin sample is about 440 nanometers. A sample of urine with bilirubin present may react with a bilirubin reagent as well as having a dark amber color. Typically, bilirubin generates a reflectance signal below approximately 510 nanometers. Urine samples with bilirubin present tend to have high reflectance signals in the blue wavelength region (e.g. below 510 nanometers) and little reflectance in the red wavelength region (e.g. above 590 nanometers). The red-green-blue color may be translated into a numeric color code, such as the RGB code.

When the specimen is urine, and when the test pad 145 has a white color before use, and the constituent of interest in the specimen is bilirubin, a suitable ratio algorithm is 1000*(red RGB code)/(blue RGB code+30). This exemplary ratio algorithm is optimized for a white test pad 145. Of course, the ratio algorithm may be modified to take into account different expected colors and/or color ranges. For example, if the test pad 145 is a different color such as red, green, blue, or a combination of colors, then the ratio algorithm may be modified to take this into account. Further, if the second sample is applied to another one of the reagent pads 140 treated with a reagent different than the reagent pad 140 to which the first sample of the specimen was applied, the ratio algorithm may be modified to take into account a different expected color or color range.

In one embodiment, the first and second samples may be read as the first and second samples pass through one or more container, passages or cuvettes which may have an optically transparent window, or be constructed of optically transparent material. For example, light of one or more wavelengths may be passed through a cuvette to the first and/or second sample and then analyzed as discussed previously. In one aspect, a flow-through cuvette may be used to measure the color of the sample. For example, the sample may be passed through a specific gravity (SG) well which may also be used to measure the sample specific gravity and clarity by light diffraction. The first and/or second sample may pass through the cuvette and the amount of light that passes through may be measured and analyzed as discussed previously.

While the inventive concepts disclosed herein will be described primarily in connection with automatic reagent analyzers using multiple-profile reagent cards, the inventive concepts disclosed herein are not limited to automatic reagent analyzers or to multiple-profile reagent cards. For example, the inventive concepts disclosed herein may be implemented with a manual analyzer, or may be implemented with an automatic reagent analyzer using a dip-and-read reagent test device, or a reel of reagent test substrate, and combinations thereof, as will be appreciated by a person of ordinary skill in the art having the benefit of the instant disclosure.

CONCLUSION

Conventionally, when detecting certain analytes, such as bilirubin, reagent analyzers produced an undesirable number of false positive results indicating the presence of a constituent, such as bilirubin, in a specimen when, in fact, bilirubin was not present. In accordance with the present disclosure, methods and systems are disclosed to verify positive readings by analyzing a sample of the specimen and reagent as well as a sample of the specimen without the reagent present. In such a way, the undesirable number of false positive results is reduced.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. A reagent analyzer, comprising:
a test analyzing mechanism configured to read at least one property of a first sample of a specimen combined with a reagent and a second sample of the specimen that is not combined with the reagent, and to output one or more signals indicative of the test analyzing mechanism reading the first sample combined with the reagent and the test analyzing mechanism reading the second sample; and
a processor coupled to the test analyzing mechanism and configured to receive the one or more signals indicative of the reading of the first sample combined with the reagent and the reading of the second sample; the processor coupled to a non-transitory computer readable medium storing computer executable code that when executed by the processor cause the processor to:
analyze the one or more signals to determine whether an analyte of interest is present in the first sample by quantifying a first predetermined property of the first sample combined with the reagent;
analyze the one or more signals to quantify a second predetermined property of the second sample; and
verify a presence of the analyte of interest in the first sample based on the quantification of the first predetermined property and the second predetermined property.

2. A reagent analyzer, comprising:
a test analyzing mechanism configured to read a first sample of a specimen combined with a reagent configured to react with the sample in a presence of an analyte of interest and a second sample of the specimen that is not combined with the reagent, and to output one or more first signals indicative of the test analyzing mechanism reading the first and second samples; and
a processor receiving the one or more signals, and executing first logic to analyze the second sample responsive to the processor determining that the analyte of interest is present in the first sample.

3. The reagent analyzer of claim 2, wherein the test analyzing mechanism includes an optical imaging system receiving one or more reflectance signals having wavelengths of light from the first sample and the second sample, and wherein one or more first signals is indicative of the optical imaging system reading the first and second samples and determining colors represented by the wavelengths of light.

4. The reagent analyzer of claim 3, wherein the optical imaging system generates one or more image having pixels with each pixel comprising information indicative of red, blue, and green color wavelength regions, the one or more image having a first region of pixels indicative of wavelengths of light reflecting from the first sample, and a second region of pixels indicative of wavelengths of light reflecting from the second sample.

5. The reagent analyzer of claim 4, wherein the analyte of interest is bilirubin.

6. The reagent analyzer of claim 5, wherein the processor executes logic to analyze the first sample to verify the presence of the analyte of interest in the first sample in comparison to a predetermined color range indicative of an expected color for an analyte-reagent reaction.

7. The reagent analyzer of claim 6, wherein the processor executes logic to analyze the second sample in comparison to the predetermined color range of the expected color of the specimen containing the analyte of interest.

8. The reagent analyzer of claim 6, wherein the processor executes logic to determine the color of the second sample and compares the color of the second sample to a known value to verify the presence of the analyte in the first sample.

9. A method comprising:
reading, with an optical imaging system of a reagent analyzer, a first sample of a specimen combined with a reagent configured to react with the specimen in a presence of an analyte of interest, and a second sample of the specimen that is not combined with the reagent;
transmitting, to a processor, one or more first signals indicative of the optical imaging system reading the first and second samples; and
executing, with the processor, first logic to analyze the second sample within the one or more first signals responsive to the processor determining that the analyte of interest is present in the first sample.

10. A method comprising:
reading, with an optical imaging system of a reagent analyzer, a first sample of a urine specimen combined with a reagent configured to react with the urine specimen in a presence of bilirubin, and a second sample of the urine specimen that is not combined with the reagent;
transmitting, to a processor, one or more first signals indicative of the optical imaging system reading the first and second samples; and
analyzing the first sample in the one or more first signals for the presence of bilirubin by the processor with first logic;
analyzing the second sample in the one or more first signals for the presence of bilirubin by the processor with second logic; and
outputting a second signal indicative of the specimen containing bilirubin responsive to the analysis of the first logic and the second logic determining the presence of bilirubin in the first and second samples.

11. The method of claim 10, wherein the step of analyzing the second sample is responsive to the presence of bilirubin being present in the first sample.

12. A method comprising:
reading, with an optical imaging system of a reagent analyzer, a first color of a first sample of a urine specimen combined on a reagent pad with a reagent configured to react with the urine specimen in a presence of bilirubin to produce a predetermined color range, and a second color of a second sample of the urine specimen on a test pad that is not combined with the reagent;
transmitting, to a processor, one or more first signals indicative of the first and second color read by the optical imaging system; and
executing, with the processor, first logic to analyze the second color of the second sample within the one or more first signals, responsive to the processor determining that the bilirubin is present in the first sample through comparing the first color to the predetermined color range.

13. The method of claim 12, wherein analyzing with the first logic compares the second color with a predetermined range indicative of expected color of the second sample of the urine specimen without the reagent when bilirubin is present.

14. The method of claim 12, wherein analyzing the second color of the second sample comprises the steps of:
translating the second color of the second sample within the one or more first signals into a color code having multiple color components;
determining a ratio of one of the color components relative to another one of the color components; and
comparing a result of the ratio with a predetermined range indicative of an expected color of the second sample of the urine specimen.

15. The method of claim 12, further comprising:
transmitting, by the processor, one or more second signals indicative of the presence of bilirubin in the urine specimen.

* * * * *